(12) United States Patent
Keacher

(10) Patent No.: US 8,233,977 B2
(45) Date of Patent: Jul. 31, 2012

(54) GRAPHICAL CONFIGURATION OF ELECTRODES FOR ELECTRICAL STIMULATION

(75) Inventor: Jeffrey T. Keacher, Stanford, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/271,525

(22) Filed: Oct. 12, 2011

(65) Prior Publication Data

US 2012/0029597 A1     Feb. 2, 2012

Related U.S. Application Data

(63) Continuation of application No. 11/698,746, filed on Jan. 26, 2007, now Pat. No. 8,082,034.

(51) Int. Cl.
     *A61N 1/00*      (2006.01)
     *A61B 5/04*      (2006.01)

(52) U.S. Cl. ............................. 607/2; 600/509; 600/512

(58) Field of Classification Search ...... 607/2; 600/509, 600/512–513
See application file for complete search history.

(56) References Cited

U.S. PATENT DOCUMENTS

| | | | |
|---|---|---|---|
| 4,793,353 A | 12/1988 | Borkan |
| 5,733,312 A | 3/1998 | Schloss et al. |
| 5,938,690 A | 8/1999 | Law et al. |
| 5,983,140 A | 11/1999 | Smith et al. |
| 6,052,624 A | 4/2000 | Mann |
| 6,106,464 A | 8/2000 | Bass et al. |
| 6,308,102 B1 | 10/2001 | Sieracki et al. |
| 6,381,496 B1 | 4/2002 | Meadows et al. |
| 6,393,325 B1 | 5/2002 | Mann et al. |
| 6,609,032 B1 | 8/2003 | Woods et al. |
| 6,622,048 B1 | 9/2003 | Mann et al. |
| 6,659,968 B1 | 12/2003 | McClure |
| 6,909,917 B2 | 6/2005 | Woods et al. |
| 7,033,326 B1 | 4/2006 | Pianca et al. |
| 7,035,690 B2 | 4/2006 | Goetz |
| 7,386,348 B2 | 6/2008 | North et al. |
| 7,657,319 B2 | 2/2010 | Goetz et al. |
| 7,676,273 B2 | 3/2010 | Goetz et al. |
| 7,822,483 B2 | 10/2010 | Stone et al. |
| 7,826,902 B2 | 11/2010 | Stone et al. |
| 7,848,802 B2 | 12/2010 | Goetz et al. |

(Continued)

FOREIGN PATENT DOCUMENTS

EP     0773038 A2     5/1997

(Continued)

OTHER PUBLICATIONS

Office Action from U.S. Appl. No. 11/999,722, dated Aug. 19, 2011, 10 pp.

(Continued)

*Primary Examiner* — Nicole F Lavert
(74) *Attorney, Agent, or Firm* — Shumaker & Sieffert, PA

(57) ABSTRACT

A device that programs a medical device includes a display and a user input device. The device displays a graphical representation of a plurality of electrodes on a medical lead implanted in the patient, and displays an active electrode template at a first position relative to the graphical representation of the electrodes. A processor of the device receives input dragging the active electrode template. In response to the input dragging the active electrode template, the processor adjusts at least one parameter of electrical stimulation delivered to the patient via the lead based on the position of the active electrode template relative to the graphical representation of the electrodes on the medical lead.

19 Claims, 9 Drawing Sheets

U.S. PATENT DOCUMENTS

| | | | |
|---|---|---|---|
| 7,933,655 | B2 | 4/2011 | Sieracki et al. |
| 8,082,034 | B2 | 12/2011 | Keacher |
| 2001/0007950 | A1 | 7/2001 | North et al. |
| 2002/0116036 | A1 | 8/2002 | Daignault, Jr. et al. |
| 2004/0034394 | A1* | 2/2004 | Woods et al. .................. 607/46 |
| 2004/0059395 | A1 | 3/2004 | North et al. |
| 2004/0215286 | A1 | 10/2004 | Stypulkowski |
| 2005/0070781 | A1 | 3/2005 | Dawant et al. |
| 2006/0017749 | A1 | 1/2006 | McIntyre et al. |
| 2006/0020297 | A1 | 1/2006 | Gerber et al. |
| 2006/0094951 | A1 | 5/2006 | Dean et al. |
| 2006/0229687 | A1 | 10/2006 | Goetz et al. |
| 2006/0259099 | A1 | 11/2006 | Goetz et al. |
| 2007/0055322 | A1 | 3/2007 | Forsberg et al. |
| 2007/0203538 | A1 | 8/2007 | Goetz et al. |
| 2007/0203540 | A1 | 8/2007 | Goetz et al. |
| 2007/0203541 | A1 | 8/2007 | Goetz et al. |
| 2007/0203543 | A1 | 8/2007 | Goetz et al. |
| 2007/0203544 | A1 | 8/2007 | Goetz et al. |
| 2007/0203545 | A1 | 8/2007 | Goetz et al. |
| 2007/0213790 | A1 | 9/2007 | Nolan et al. |
| 2008/0103407 | A1 | 5/2008 | Bolea et al. |
| 2008/0154340 | A1 | 6/2008 | Goetz et al. |
| 2008/0163097 | A1 | 7/2008 | Goetz et al. |
| 2008/0215118 | A1 | 9/2008 | Goetz et al. |

FOREIGN PATENT DOCUMENTS

| | | |
|---|---|---|
| WO | WO 01/83028 A1 | 11/2001 |
| WO | WO 2004/041351 A1 | 5/2004 |
| WO | WO 2004/045711 A1 | 6/2004 |

OTHER PUBLICATIONS

Response to Office Action dated Aug. 19, 2011, from U.S. Appl. No. 11/999,722, filed Nov. 21, 2011, 14 pp.

Office Action from U.S. Appl. No. 11/999,726, dated Sep. 7, 2011, 16 pp.

Response to Office Action dated Sep. 7, 2011, from U.S. Appl. No. 11/999,726, filed Nov. 7, 2011, 15 pp.

Office Action from U.S. Appl. No. 11/999,735, dated Sep. 7, 2011, 12 pp.

Popovic, "Modular transcutaneous functional electrical stimulation system," Medical Engineering & Physics 27 (2005): 81-92.

Response to Office action for U.S. Appl. No. 11/999,735, filed Jan. 4, 2012, 12 pages.

Honeywell Inc. Systems and Research Division Research Department, "Experimental Evaluation of Symbolic and Pictorial Displays for Submarine Control," U.S. Dept. of Commerce Nat'l Technical Info. Service, Sep. 1965, 122 pages.

O'Halloran et al., "Modified implanted drop foot stimulator system with graphical user interface for customised stimulation pulse-width profiles," Medical & Biological Engineering and Computing, vol. 41, 2003, pp. 701-709.

North et al., "Automated, Patient-Interactive, Spinal Cord Stimulator Adjustment: Randomized Controlled Trial," Neurosurgery, vol. 52, No. 3, Mar. 2003, pp. 572-580.

International Preliminary Report on Patentability for international application No. PCT/US2007/008697, mailed Apr. 23, 2009, 8 pages.

Reply to Written Opinion for international patent application No. PCT/US2007/008697, filed Jun. 12, 2008, 8 pp.

International Search Report and Written Opinion of international application No. PCT/US2007/008697, mailed Oct. 12, 2007, 12 pages.

International Preliminary Report on Patentability for international application No. PCT/US2007/024977, dated Nov. 14, 2008, 11 pp.

International Search Report and Written Opinion for international application No. PCT/US2007/024977, dated Jul. 8, 2008, 12 pp.

Reply to Written Opinion for international application No. PCT/US2007/024977, filed Oct. 3, 2008, 11 pp.

Examination Report from European application No. 07862567.0, dated Oct. 19, 2009, 2 pp.

Reply to Written Opinion for international application No. PCT/US2007/024969, filed Oct. 21, 2008, 10 pp.

International Search Report and Written Opinion for international application No. PCT/US2007/024969, dated Jul. 21, 2008, 13 pp.

International Preliminary Report on Patentability for international application No. PCT/US2007/024969, dated Dec. 3, 2008, 11 pp.

International Preliminary Report on Patentability for international application No. PCT/US2007/024962, dated Mar. 5, 2009, 7 pp.

Reply to Written Opinion for international application No. PCT/US2007/024962, filed Dec. 30, 2008, 5 pp.

International Search Report and Written Opinion for international application No. PCT/US2007/024962, dated Oct. 1, 2008, 12 pp.

Office Action from U.S. Appl. No. 11/698,746, dated May 15, 2009, 7 pp.

Response to Office Action dated May 15, 2009, from U.S. Appl. No. 11/698,746, filed Aug. 14, 2009, 12 pp.

Office Action from U.S. Appl. No. 11/698,746, dated Mar. 2, 2010, 7 pp.

Response to Office Action dated Mar. 2, 2010, from U.S. Appl. No. 11/698,746, filed Jun. 2, 2010, 15 pp.

Final Office Action from U.S. Appl. No. 11/698,746, dated Oct. 7, 2010, 10 pp.

Response to Final Office Action dated Oct. 7, 2010, from U.S. Appl. No. 11/698,746, filed Dec. 7, 2010, 6 pp.

Pre-Appeal Brief Request for Review from U.S. Appl. No. 11/698,746, filed Mar. 9, 2011, 5 pp.

Notice of Panel Decision from Pre-Appeal Brief Review, from U.S. Appl. No. 11/698,746, dated May 6, 2011, 2 pp.

Notice of Allowance from U.S. Appl. No. 11/698,746, dated Jul. 8, 2011, 10 pp.

Amendment after Notice of Allowance (Rule 312) from U.S. Appl. No. 11/698,746, filed Oct. 6, 2011, 15 pp.

Response to Rule 312 from U.S. Appl. No. 11/698,746, dated Nov. 21, 2011, 2 pp.

Final Office Action from U.S. Appl. No. 11/999,722, dated Apr. 24, 2012, 9 pp.

Office Action from U.S. Appl. No. 11/999,735, May 10, 2010, 11 pp.

Response to Office Action dated May 10, 2010, from U.S. Appl. No. 11/999,735, filed Aug. 10, 2010, 13 pp.

Final Office Action from U.S. Appl. No. 11/999,735, Oct. 25, 2010, 8 pp.

Response to Final Office Action Oct. 25, 2010, from U.S. Appl. No. 11/999,735, filed Dec. 23, 2010, 14 pp.

Advisory Action dated Jan. 20, 2011, from U.S. Appl. No. 11/999,735, 3 pp.

Response to Advisory Action dated Jan. 20, 2011, from U.S. Appl. No. 11/999,735, filed Feb. 24, 2011, 17 pp.

Office Action from U.S. Appl. No. 11/999,735, dated Sep. 7, 2011, 9 pp.

Response to Office Action dated Sep. 7, 2011, from U.S. Appl. No. 11/999,735, filed Jan. 4, 2012, 13 pp.

Final Office Action from U.S. Appl. No. 11/999,735, Feb. 1, 2012, 10 pp.

Response to Final Office Action dated Feb. 1, 2012, from U.S. Appl. No. 11/999,735, filed Apr. 2, 2012, 6 pp.

Advisory Action dated Apr. 11, 2012, from U.S. Appl. No. 11/999,735, 3 pp.

Office Action from U.S. Appl. No. 11/999,726, dated Oct. 4, 2010, 15 pp.

Response to Office Action dated Oct. 4, 2010, from U.S. Appl. No. 11/999,726, filed Jan. 4, 2011, 20 pp.

Office Action from U.S. Appl. No. 11/999,726, dated Apr. 6, 2011, 10 pp.

Response to Office Action dated Apr. 6, 2011, from U.S. Appl. No. 11/999,726, filed Jul. 6, 2011, 20 pp.

Final Office Action from U.S. Appl. No. 11/999,726, dated Sep. 7, 2011, 16 pp.

Response to Final Office Action dated Sep. 7, 2011, from U.S. Appl. No. 11/999,726, filed Nov. 7, 2011, 20 pp.

Advisory Action from U.S. Appl. No. 11/999,726, dated Nov. 25, 2011, 3 pp.

Final office action for U.S. Appl. No. 11/999,722, mailed Apr. 24, 2012, 9 pages.

* cited by examiner

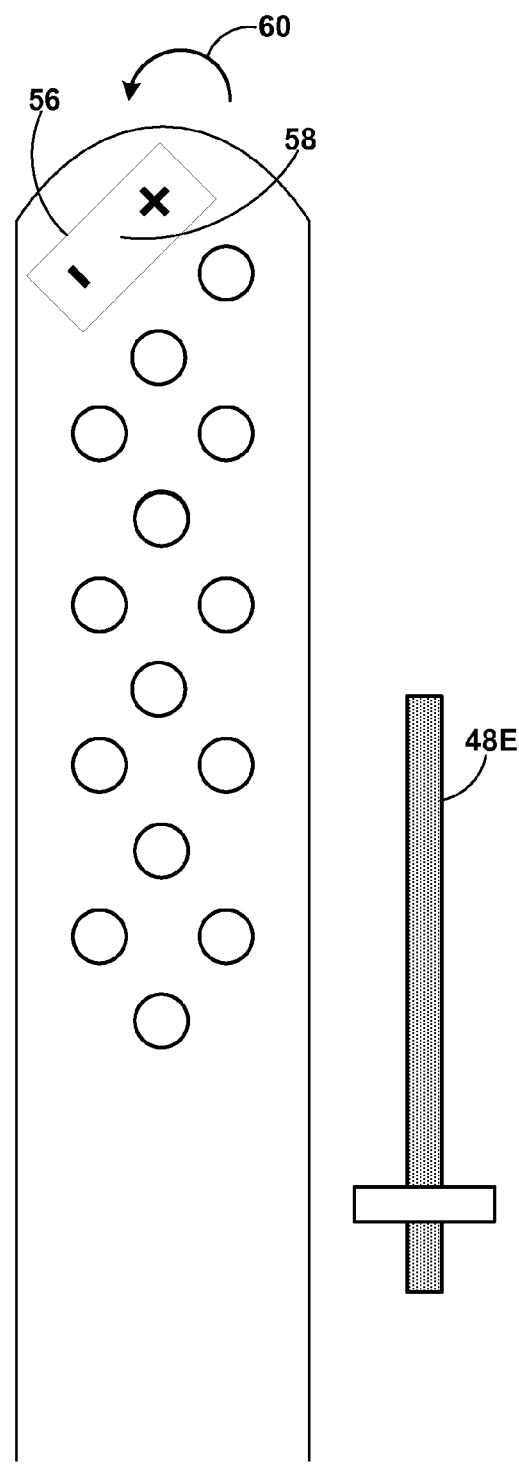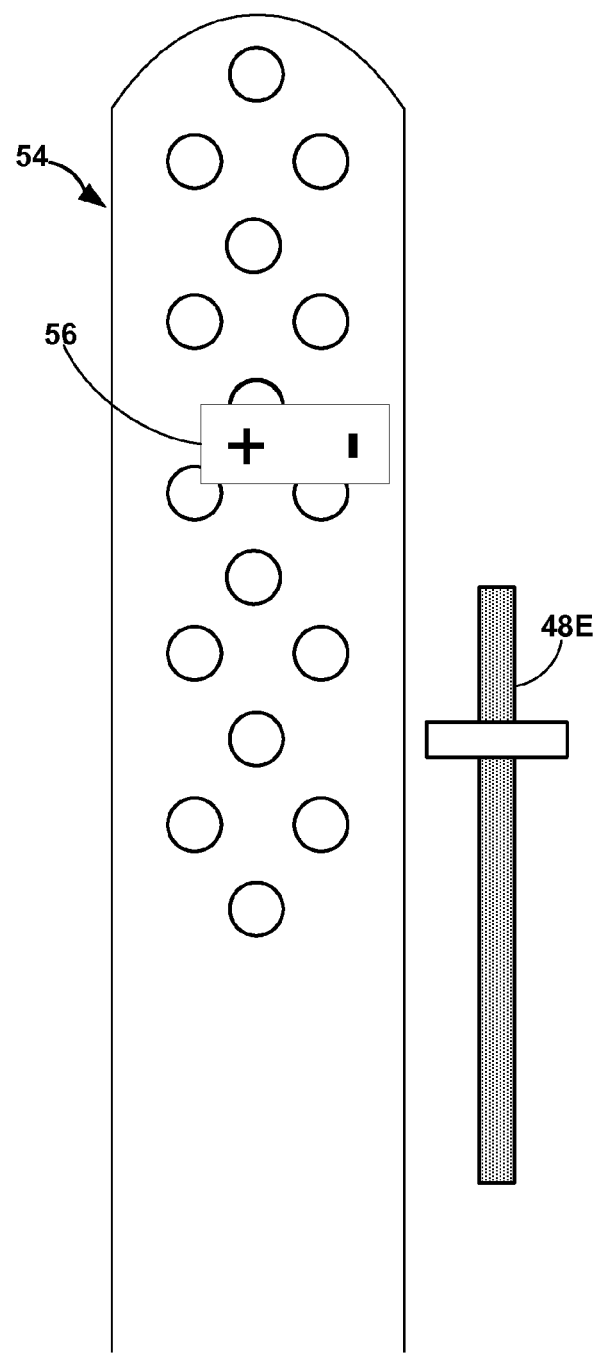
FIG. 6A  FIG. 6B

GRAPHICAL CONFIGURATION OF ELECTRODES FOR ELECTRICAL STIMULATION

This application is a continuation of U.S. application Ser. No. 11/698,746, filed Jan. 26, 2007, issued as U.S. Pat. No. 8,082,034 on Dec. 20, 2011, the entire content of which is incorporated herein by reference.

TECHNICAL FIELD

The invention relates to electrical stimulation therapy and, more particularly, to programming electrical stimulation therapy for a patient.

BACKGROUND

Implantable medical devices may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. An implantable medical device may deliver electrical stimulation therapy via leads that include electrodes, which may, for example, be located proximate to the spinal cord, pelvic nerves, stomach, or within the brain of a patient. In general, implantable medical devices deliver electrical stimulation therapy in the form of electrical pulses or substantially continuous-time signals.

A clinician may select values for a number of programmable parameters in order to define the electrical stimulation therapy to be delivered to a patient. For example, in the case of stimulation delivered in the form of electrical pulses, the clinician may select an amplitude, which may be a current or voltage amplitude, and pulse width for a stimulation waveform to be delivered to the patient, as well as a rate at which the pulses are to be delivered to the patient. The clinician may also select particular electrodes within an electrode set to be used to deliver the pulses and the polarities of the selected electrodes. A selection of electrodes from among those available on one or more leads and their polarities may be referred to as an electrode configuration. A group of parameter values, which may include an electrode configuration, may be referred to as a program in the sense that they drive the electrical stimulation therapy to be delivered to the patient.

The process of selecting values for the parameters can be time consuming, and may require a great deal of trial and error before a desirable program is discovered. The "best" program may be a program that best balances greater clinical efficacy and minimal side effects experienced by the patient. In addition, power consumption by a medical device may be different during delivery of therapy according to different programs.

The clinician typically needs to test a large number of possible electrode configurations in order to identify one or more desirable electrode configurations. As a portion of the overall parameter selection process, the process of selecting electrodes and the polarities of the electrodes, i.e., electrode configurations, can be particularly time-consuming and tedious. In some cases, the clinician may test electrode configurations by manually specifying each configuration based on intuition or some idiosyncratic methodology. The clinician may then record notes on the efficacy and side effects of each configuration after delivery of stimulation via that configuration. In this manner, the clinician is able to later compare and select from the tested configurations. As an example of the magnitude of the task, an implantable electrical stimulator commonly delivers spinal cord stimulation (SCS) therapy to a patient via two leads that include eight electrodes per lead, which equates to over 43 million potential electrode configurations.

In order to improve the efficacy of electrical stimulation therapy, implantable medical devices have grown in capability and complexity. Modern implantable medical devices tend to have larger numbers of potential electrode configurations, larger ranges for other parameters, and the ability to substantially simultaneously deliver multiple therapy programs by interleaving stimulation pulses in time. Although these factors increase the clinician's ability to tailor therapy for a particular patient or disease state, the burden involved in optimizing device parameters has similarly increased.

SUMMARY

In general, the invention to directed toward techniques for graphically programming delivery of electrical stimulation to a patient by a medical device. More particularly, the invention is directed to techniques for adjusting one or more stimulation parameters, e.g., of a program, by manipulating the position of an active electrode template relative to a graphical representation of electrodes implanted within a patient on one or more leads. The active electrode template may comprise one or more anodes and at one or more cathodes and define a spatial relationship of the one or more anodes and one or more cathodes.

Using an input device, such as a mouse, other pointing device, or touch screen, a user may drag the active electrode template to a variety of positions relative to the graphical representation of the implanted electrodes. The stimulation parameters are adjusted based on the position of the active electrode template relative to the graphical representation of the active electrode, and may be adjusted when the active electrode template is dropped at a new position, or a plurality of times while the template is being dragged. In some embodiments, dragging the active electrode template may include rotating the template about an axis point.

Adjusting stimulation parameters based on the position of the active electrode template may include adjusting the electrode configuration, e.g., adjusting which of the implanted electrodes are active, the potentials of individual electrodes, and/or polarities of active electrodes. Adjusting stimulation parameters based on the position of the active electrode template may additionally or alternatively include adjusting other parameters, such as pulse amplitude, width and rate. In other embodiments, parameters, such as amplitude, may be adjusted independently by the user, e.g., during or between movements of the active electrode template.

In one embodiment, the invention is directed to a method comprising displaying a graphical representation of a plurality of electrodes implanted within a patient on at least one medical lead, and displaying an active electrode template at a first position relative to the graphical representation of the electrodes, the active electrode template including one or more anodes and one or more cathodes and defining a spatial relationship of the one or more anodes and one or more cathodes. The method further comprises receiving input from a user dragging the active electrode template to a second position relative to the graphical representation of the electrodes, and, in response to the input dragging the active electrode template, adjusting at least one parameter of electrical stimulation delivered to the patient via at least a subset of the implanted electrodes based on the second position of the active electrode template relative to the graphical representation of the electrodes on the stimulation lead.

In another embodiment, the invention is directed to a device comprising a display that displays a graphical representation of a plurality of electrodes on at least one medical lead implanted in a patient, and displays an active electrode template at a first position relative to the graphical representation of the electrodes, the graphical representation of the active electrode template including one or more anodes and one or more cathodes and defining a spatial relationship of the one or more anodes and one or more cathodes. The device further comprises a user input device, and a processor that receives input dragging the active electrode template to a second position relative to the graphical representation of the electrodes on the medical lead via the user input device, and, in response to the input dragging the active electrode template, adjusts at least one parameter of electrical stimulation delivered to the patient via at least a subset of the implanted electrodes based on the second position of the active electrode template relative to the graphical representation of the electrodes on the stimulation lead.

In another embodiment, the invention is directed to a computer-readable medium containing instructions. The instructions cause a processor to control display of a graphical representation of a medical lead implanted within a patient, the graphical representation of the medical lead including a graphical representation of a plurality of electrodes on the medical lead, and control display of an active electrode template at a first position relative to the graphical representation of the electrodes, the graphical representation of the active electrode template including one or more anodes and one or more cathodes and defining a spatial relationship of the one or more anodes and one or more cathodes. The instructions further cause the processor to receive input from a user dragging the active electrode template to a second position relative to the graphical representation of the electrodes on the medical lead, and, in response to the input dragging the active electrode template, adjust at least one parameter of electrical stimulation delivered to the patient via at least a subset of the implanted electrodes based on the second position of the active electrode template relative to the graphical representation of the electrodes on the stimulation lead.

Embodiments of the invention may provide advantages. For example, adjusting stimulation parameters such as electrode configuration by positioning an active electrode template may facilitate more rapid evaluation of a plurality of parameter values than is possible with manual selection of each parameter value to test; particularly in embodiments where parameter values are adjusted during dragging of the active electrode template. Further, adjusting electrode configurations based on relative positions of graphical representations in response to manipulation of a graphical representation may be more intuitive for clinicians and other users than adjusting electrode configuration based on a directional input.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 6A illustrates another graphical representation of implanted electrodes and an initial active electrode template position.

FIG. 6B illustrates a second position of the electrode template relative to the graphical representation of electrodes in FIG. 6A.

DETAILED DESCRIPTION

Figure 1:
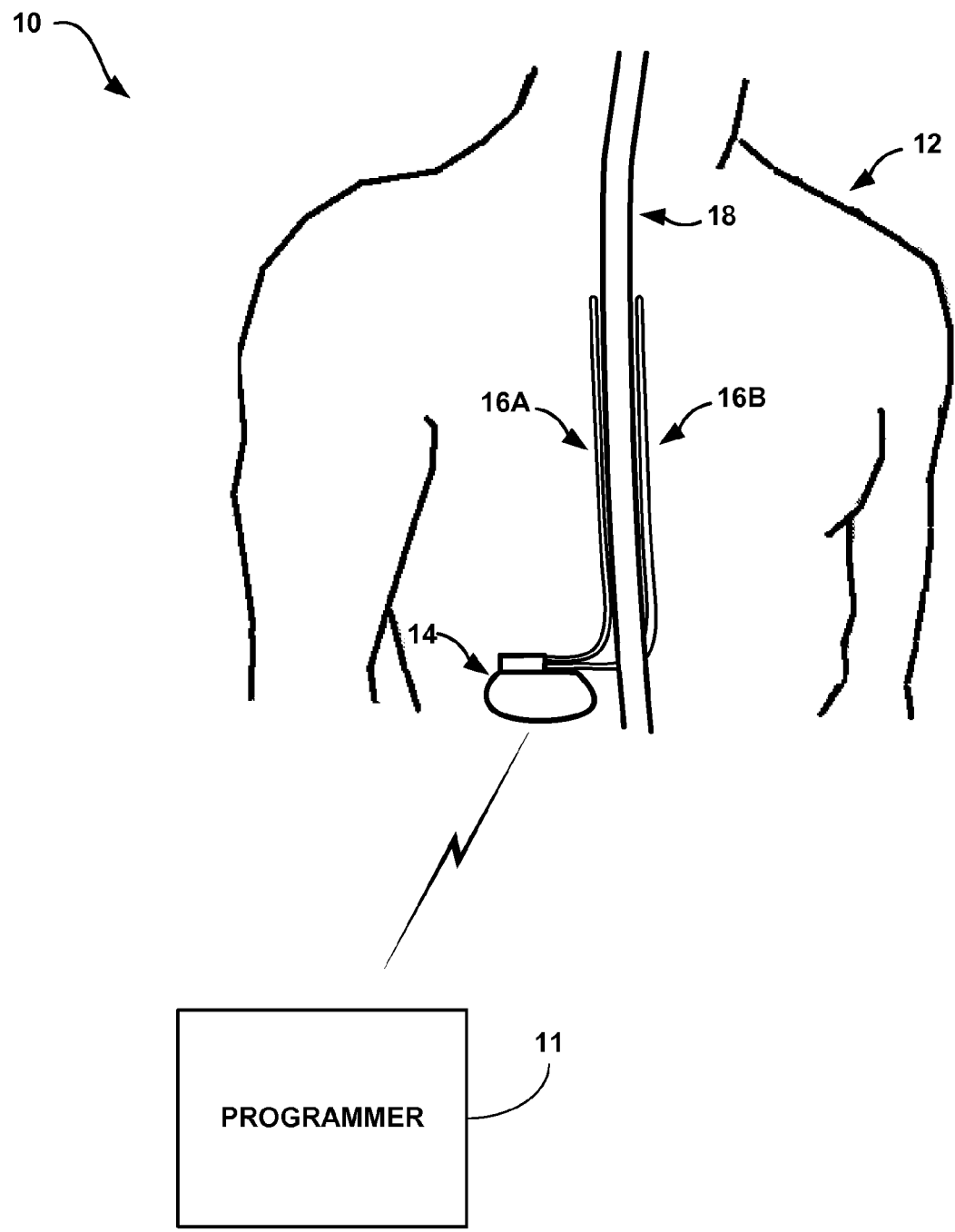
FIG. 1 is a schematic diagram illustrating an example system for delivery and programming of electrical stimulation therapy.

FIG. 1 is a schematic diagram illustrating an example system 10 for programming electrical stimulation therapy and for delivering electrical stimulation therapy to a patient 12. System 10 includes an implantable medical device (IMD) 14 that delivers electrical stimulation therapy to patient 12 and a programmer 11 for programming IMD 14. IMD 14 may also be referred to as an electrical stimulator, or a pulse or signal generator. In the embodiment shown in FIG. 1, IMD 14 may also be referred to as a neurostimulator.

IMD 14 delivers neurostimulation therapy to patient 12 via leads 16A and 16B (collectively "leads 16"). Although two leads 16 are shown for purposes of illustration, the invention is not limited to the combination of leads 16 shown in FIG. 1. For example, system 10 may include only a single lead or more than two leads. Leads 16 may, as shown in FIG. 1, be implanted proximate to spinal cord 18 of patient 12 to deliver spinal cord stimulation therapy to patient 12. Spinal cord stimulation may be used, for example, to reduce pain experienced by patient 12. Although an IMD 14 is described for purposes of illustration, various embodiments of this disclosure also may be applicable to external stimulators that reside outside the patient's body, and deliver electrical stimulation therapy using one or more implanted leads deployed via a percutaneous port, or transcutaneously via one or more external electrodes.

Leads 16 may also be located at other nerve or tissue sites within patient 12. In addition, system 10 is not limited to spinal cord stimulation, and may be applicable to other electrical stimulation applications including pelvic floor stimulation, deep brain stimulation, cortical surface stimulation, neuronal ganglion stimulation, gastric stimulation, peripheral nerve stimulation, or subcutaneous stimulation. Such therapy applications may be targeted to a variety of disorders such as chronic pain, peripheral vascular disease, angina, headache, tremor, depression, Parkinson's disease, epilepsy, urinary or fecal incontinence, sexual dysfunction, obesity, or gastroparesis.

IMD 14 delivers neurostimulation therapy to patient 12 according to one or more therapy programs. A therapy program may specify an electrode configuration and values for a number of other parameters that define the electrical stimulation delivered via the electrode configuration. The other parameters may include voltage or current stimulation pulse amplitudes, pulse widths, and pulse rates, as well as other parameters such as duration or duty cycle. Leads 16 each include one or more electrodes (not shown in FIG. 1). The program further specifies, as a stimulation parameter, the electrode configuration in terms of electrodes that have been selected to deliver pulses according to the program, i.e., the active subset of the electrodes located on leads 16, and the polarities of the active electrodes.

Two of the parameters which may be significant for optimization of electrical stimulation therapy are the electrode configuration and the stimulation amplitude. The selection of electrodes is strongly correlated which tissues are stimulated and, therefore, which physiological effects are perceived. Stimulation amplitude is a significant factor in the intensity and the extent of those effects.

A programmer user, such as a clinician or patient 12, may use programmer 11 to program stimulation therapy for patient 12. In particular, the user may use programmer 11 to create stimulation programs and update the stimulation programs delivered by IMD 14. As part of the program creation process, programmer 11 may allow the user to evaluate various combinations of values for various stimulation parameters, including electrode configurations, i.e., programs, in terms of, for example, symptom relief, coverage area relative to symptom area, and lack of side effects. Programmer 11 may also allow the user to identify programs that enable IMD 14 to deliver effective therapy with desirable device performance characteristics, e.g., low battery consumption.

Programmer 11 controls IMD 14, e.g., by instructions delivered via wireless telemetry, to test parameter values in order to allow a user to identify desirable combinations. For example, programmer 11 may control IMD 14 to test a number of electrode configurations, and allows the user to select particular electrode configurations that provide efficacious results. Programmer 11 may test electrode configurations in response user input.

Programmer 11 may communicate with IMD 14 via wireless telemetry techniques known in the art. For example, programmer 11 may communicate with IMD 14 via an RF telemetry head (not shown) using near or far-field techniques, or by other local wireless communication techniques, such as communication according to the Bluetooth protocol. Information identifying desirable electrode configurations and other parameters identified by the clinician may be stored as part of stimulation therapy programs. Programs created by the clinician using programmer 11 may be transmitted to IMD 14 via telemetry, and/or may be transmitted to another programmer (not shown), e.g., a patient programmer that is used by patient 12 to control the delivery of stimulation by IMD 14 during daily use.

Programmer 11 may include different programming modes. In one programming mode, programmer 11 supports testing of different electrode configurations and/or other stimulation parameters. In this test mode, programmer 11 may receive user input and transmit programming signals to IMD 14 to repeatedly change the electrode configurations, other stimulation parameters, or both, based on the user input. In another programming mode, programmer 11 may transmit one or more programs or groups of programs to IMD 14 for longer term storage and operation of IMD 14. Such programs and program groups may specify electrode configurations and stimulation parameters selected based on the results obtained during the test mode. IMD 14 or a patient programmer may store the identified programs or groups within internal memory.

Stimulation parameter testing need not be confined to a single session, and need not occur in a clinic setting. For a variety of reasons, current programs may become less effective while other stimulation programs previously deemed ineffective may offer more effective therapy. To overcome these physiological changes, patient 12 may repeat stimulation parameter testing when the current therapy no longer provides relief. Alternatively, IMD 14 or a patient programmer used by patient 12 may prompt patient 12 to repeat stimulation parameter testing upon unusual stimulation activity or a programmed schedule. Patient 12 may perform testing according to the techniques described herein using programmer 11, a patient programmer associated with patient 12, or any other computer device. Thus, the techniques described herein are not limited to implementation via a dedicated clinician programmer.

Although programmer 11 is described as an individual unit, programmer 11 may instead be a touch screen display or other device that interfaces with larger computer or remote server. For example, programmer 11 may be a virtual programmer that provides a user interface through the touch screen or other input device. Operation of a virtual programmer may be substantially similar to an individual, or standalone, programmer.

Figure 2:
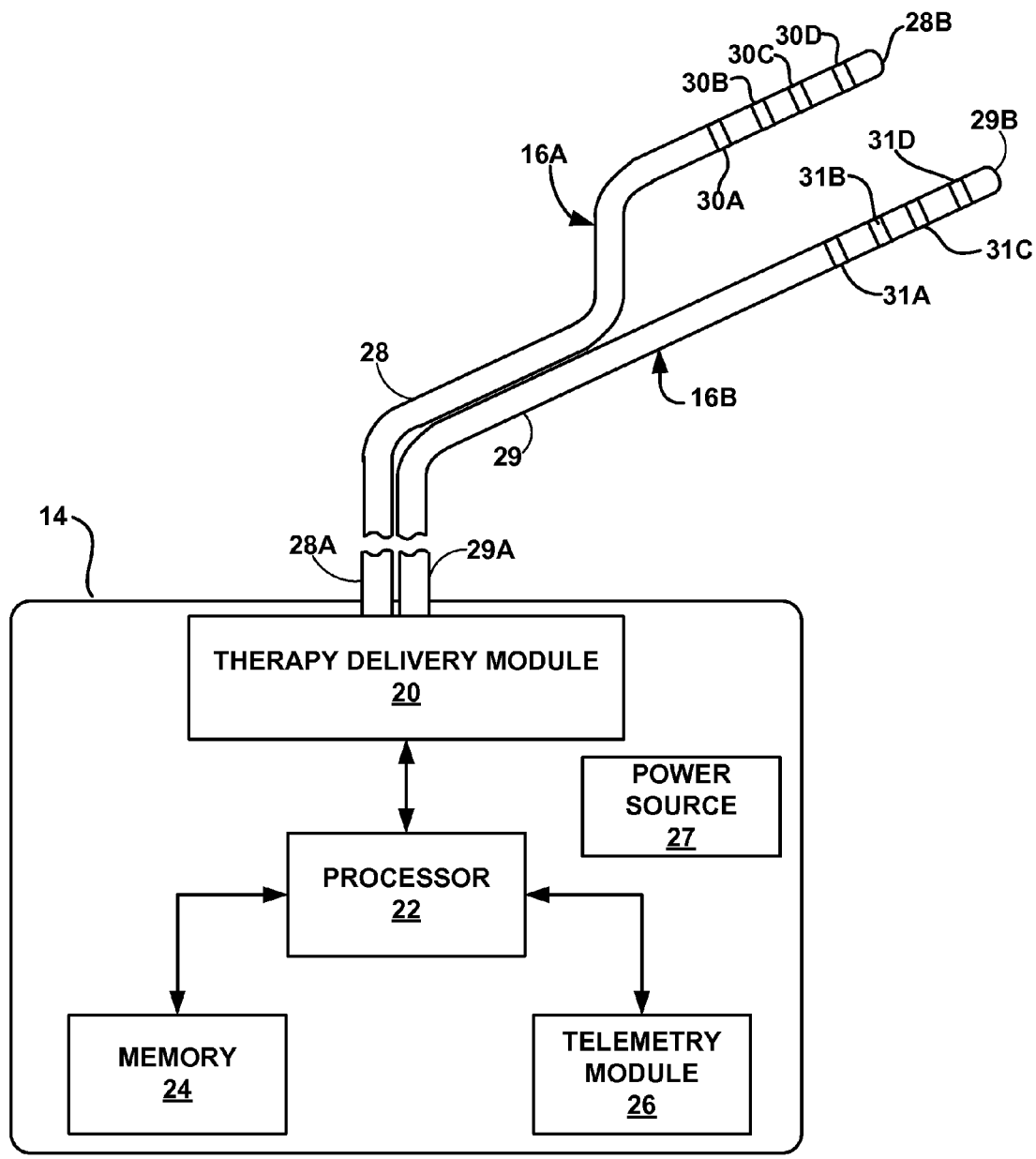
FIG. 2 is a schematic block diagram illustrating various components of an example implantable medical device and two implantable leads.

FIG. 2 is a schematic block diagram illustrating various components of IMD 14 and implantable leads 16. IMD 14 includes therapy delivery module 20, processor 22, memory 24, telemetry module 26, and power source 27. In some embodiments, IMD 14 may also include a sensing circuit (not shown in FIG. 2). Implantable lead 16A includes lead body 28 extending between proximal end 28A and distal end 28B. Similarly, implantable lead 16B includes lead body 29 extending between proximal end 29A and distal end 29B. Lead bodies 28 and 29 may be, as examples, cylindrical or may be paddle-shaped (i.e., a "paddle" lead).

Electrodes 30A, 30B, 30C, and 30D (collectively "electrodes 30") are disposed on lead body 28 adjacent to distal end 28B of lead body 28. Electrodes 31A, 31B, 31C, and 31D (collectively "electrodes 31") are disposed on lead body 29 adjacent to distal end 29B of lead body 29. The configuration, type, and number of electrodes 30 and 31 illustrated in FIG. 2 are merely exemplary. In some embodiments, electrodes 30 and 31 may be ring electrodes. In other embodiments, electrodes 30 and 31 may be segmented or partial ring electrodes, each of which extends along an arc less than 360 degrees (e.g., 90-120 degrees) around the periphery of lead bodies 28 and 29, respectively.

IMD 14 delivers stimulation therapy to target tissue sites proximal to distal ends 28B and 29B of leads 16 via electrodes 30 and 31, respectively. Electrodes 30 and 31 are electrically coupled to a therapy delivery module 20 of IMD 14 via conductors within lead bodies 28 and 29, respectively. More specifically, proximal end 28A of lead body 28 includes contacts (not shown) to electrically couple electrodes 30 directly to IMD 14 or indirectly to IMD 14, e.g., via a lead extension. Similarly, proximal end 29A of lead body 29 includes contacts (not shown) to electrically couple electrodes 31 directly or indirectly to IMD 14. In one embodiment, an implantable signal generator or other stimulation circuitry within therapy delivery module 20 delivers electrical signals (e.g., pulses or substantially continuous-time signals, such as sinusoidal signals) to target stimulation sites proximal to distal ends 28B and 29B of leads 16 via at least some of electrodes 30 and 31, respectively, under the control of a processor 22. As described in U.S. patent application Ser. No. 11/401,100, which is incorporated herein by reference in its entirety, stimulation circuitry within an IMD may be, in some examples, a single stimulation pulse generator, e.g., a single channel pulse generator connectable to different combinations of electrodes via a switch device or matrix.

IMD 14 may include a power source 27. Power source 27 may take the form of a small, rechargeable or non-rechargeable battery, or an inductive power interface that transcutaneously receives inductively coupled energy. In the case of a rechargeable battery, power source 27 similarly may include an inductive power interface for transcutaneous transfer of recharge power.

The stimulation energy generated by therapy delivery module 20 may be formulated as neurostimulation energy, e.g., for treatment of any of a variety of neurological disorders, or disorders influenced by patient neurological response. The signals may be delivered from therapy delivery module 20 to electrodes 30 and 31 via a switch matrix and conductors carried by leads 16 and electrically coupled to electrodes 30 and 31.

Processor 22 may include any one or more microprocessors, controllers, digital signal processors (DSPs), application specific integrated circuits (ASICs), field-programmable gate arrays (FPGAs), discrete logic circuitry, or the like. Processor 22 controls the implantable signal generator within therapy delivery module 20 to deliver electrical stimulation according to stimulation parameters specified by one or more selected programs. Specifically, processor 22 controls therapy delivery module 20 to deliver electrical signals with selected amplitudes, pulse widths (if applicable), and rates specified by the programs. In addition, processor 22 may also control therapy delivery module 20 to deliver the stimulation signals via selected subsets of electrodes 30 or 31 with selected polarities, as specified by electrode configurations of the selected programs. For example, electrodes 30 may be combined in various bipolar or multi-polar combinations to deliver stimulation energy to selected sites, such as nerve sites adjacent an occipital nerve, spinal column, pelvic floor nerve sites, or cranial nerve sites. Electrodes 31 may also be combined in various bipolar or multi-polar combinations to deliver stimulation energy to selected sites, such as nerve sites adjacent the spinal column, pelvic floor nerve sites, or cranial nerve sites.

Processor 22 may also control therapy delivery module 20 to deliver each signal according to a different program, thereby interleaving programs to simultaneously treat different symptoms or provide a combined therapeutic effect. The different programs may be grouped as a "program group," the programs of which are intended to be delivered substantially simultaneously, e.g., by interleaved delivery.

Memory 24 of IMD 14 may include any volatile or non-volatile media, such as a random access memory (RAM), read-only memory (ROM), non-volatile RAM (NVRAM), electronically erasable programmable ROM (EEPROM), flash memory, or the like. In some embodiments, memory 24 of IMD 14 may store multiple sets of stimulation parameters, i.e., programs, that are available to be selected by patient 12, e.g., using programmer 11 (FIG. 1) or a patient programmer, for delivery of neurostimulation therapy. Memory 24 may also stores program instructions that, when executed by processor 22, cause IMD 14 to deliver neurostimulation therapy. Accordingly, computer-readable media storing instructions may be provided to cause processor 22 to provide functionality as described herein.

Figure 3:
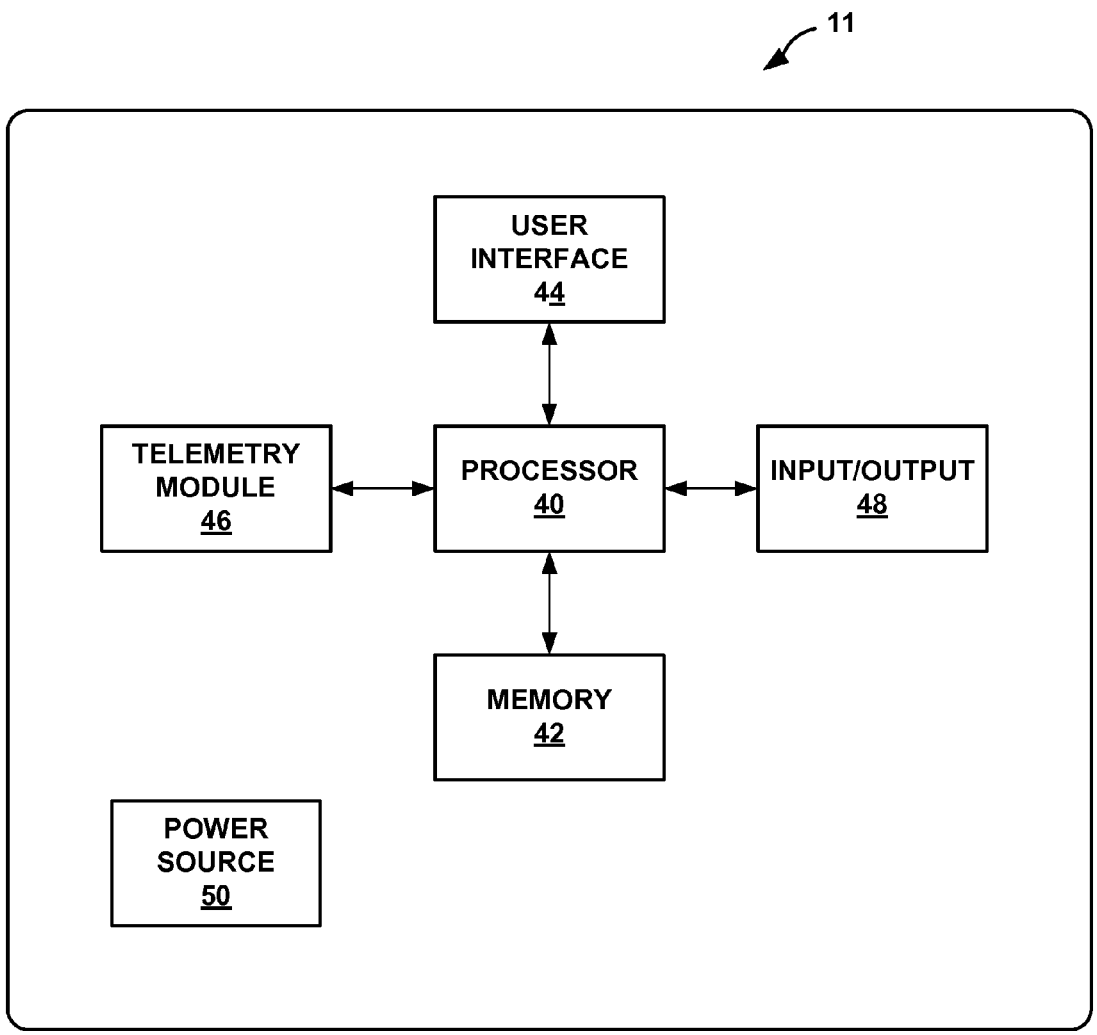
FIG. 3 is a block diagram illustrating an example configuration of a programmer.

FIG. 3 is a block diagram illustrating an example configuration of programmer 11. Programmer 11 includes processor 40, memory 42, user interface 44, telemetry module 46, input/output 48, and power source 50. A user may interact with a processor 40 via a user interface 44 in order to identify efficacious programs, e.g., electrode configurations and other therapy parameters. As will be described in further detail below, user interface 44 may include a display, graphical user interface (GUI), and/or one or more input devices. Processor 40 may include a microprocessor, a microcontroller, a DSP, an ASIC, an FPGA, or other equivalent discrete or integrated logic circuitry.

Memory 42 of programmer 11 may include program instructions that, when executed by processor 40, cause programmer 11 to perform various functions ascribed herein to programmer 11. Memory 42 may include any volatile, non-volatile, magnetic, optical, or electrical media, such as RAM, ROM, NVRAM, EEPROM, flash memory, or any other digital media.

Processor 40 may control IMD 14 to deliver stimulation therapy to patient 12 (FIG. 1). In particular, processor 40 may transmit programming signals to IMD 14 (FIG. 1) via telemetry circuit 46. Additionally, processor 40 may transmit one or more programs or program groups created by a clinician or other qualified individual to IMD 14 (FIG. 1) via telemetry circuit 46, or to another programmer used by patient 12 (FIG. 1) to control delivery of stimulation therapy via input/output circuitry 48. Input/output circuitry 48 may include transceivers for wireless communication, appropriate ports for wired communication or communication via removable electrical media, or appropriate drives for communication via removable magnetic or optical media.

Power source 50 may take the form of a small, rechargeable or non-rechargeable battery, or an inductive power interface that transcutaneously receives inductively coupled energy. In the case of a rechargeable battery, power source 50 similarly may include an inductive power interface for transcutaneous transfer of recharge power.

Figure 4:
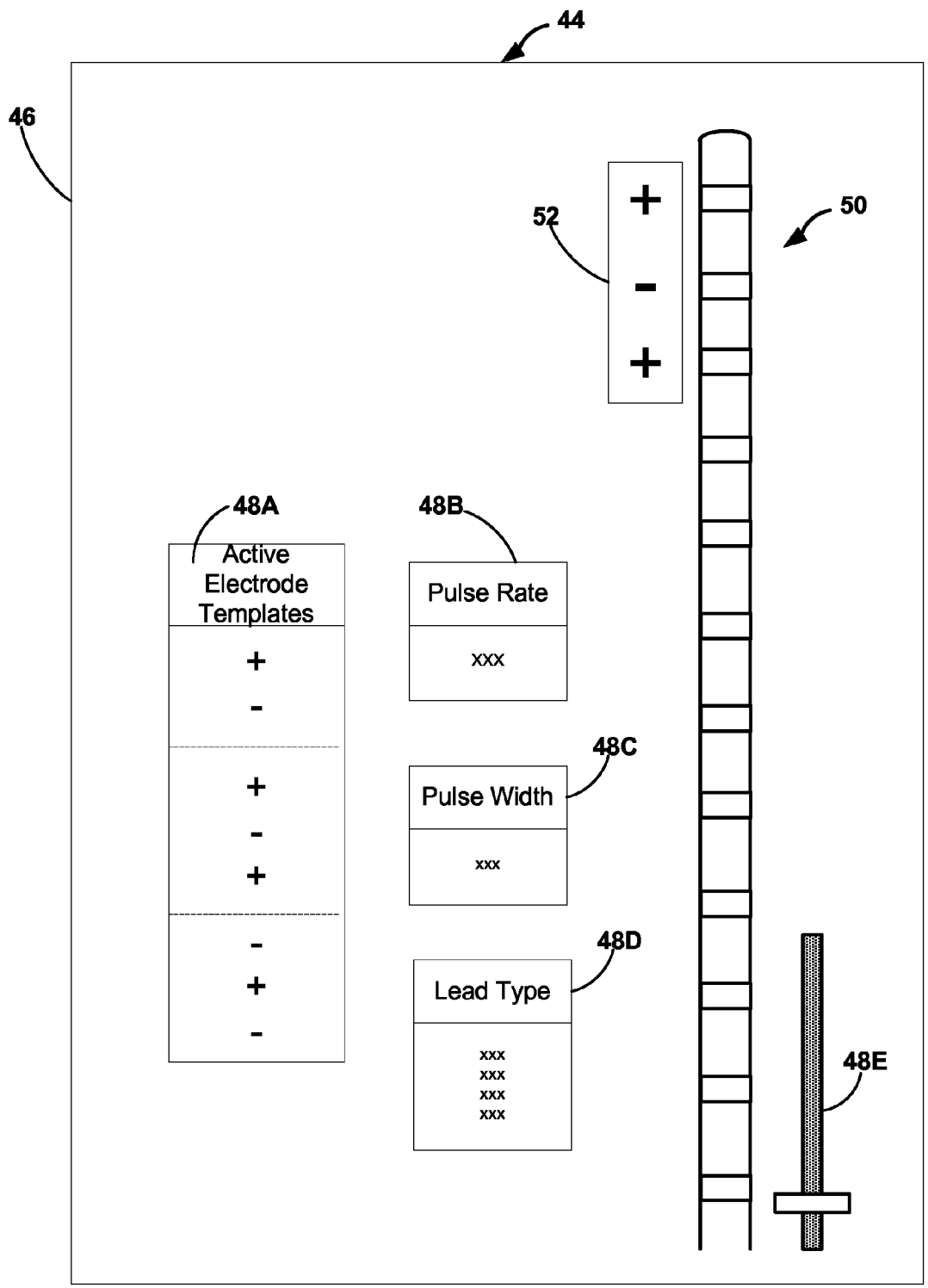
FIG. 4 illustrates an example user interface provided on a programmer.

FIG. 4 illustrates one embodiment of user interface 44 that may be provided on programmer 11 (FIG. 1). In the illustrated embodiment, user interface 44 includes display 46, therapy parameter input mechanisms 48A-48E (collectively therapy parameter input mechanisms 48), and a graphical representation 50 of electrodes implanted within patient 12 (in this case on a single lead). Therapy parameter input mechanisms 48 may include slider bars, text boxes, or any other input media. Additionally, a user may interact with therapy parameter input mechanisms 48 via a mouse, keyboard, stylus, or any other user input device. Therapy parameter input mechanisms 48 may allow a user to specify or update parameters such as pulse rate (via input mechanism 48B), pulse width (via input mechanism 48C), amplitude, e.g., voltage or current amplitude (via input mechanism 48E), or other therapy parameters.

Therapy parameter input mechanism 48D may also allow a user to specify or select a type of lead or leads to be programmed. For example, the lead type may be defined by the shape of the lead body (e.g., cylindrical or paddle), the type of electrodes (e.g., ring, segmented, or both), the number of electrodes, and/or the number of rows and/or columns of electrodes. The lead type selected may be representative of the electrodes implanted in the patient (e.g., patient 12 of FIG. 1). Additionally, for patients with multiple leads, multiple leads may be selected or each lead may be selected and programmed individually. In either case, an indicator may help ensure that the user is informed of which lead is being programmed. In some embodiments, a user may select a subset of electrodes on one or more leads and limit programming to the selected subset. The user may select which lead and/or which electrodes to program via user interface 44.

Graphical representation 50 of the implanted electrodes may be displayed by programmer 11 in response to lead type selection via input mechanism 48D. In other embodiments, graphical representation 50 may be updated based on the lead type selected via input mechanism 48D. For example, graphical representation 50 may initially display a lead type, such as a commonly-used or recently-used lead type, and graphical representation 50 may be updated based on input received via input mechanism 48D.

An active electrode template may be selected via input mechanism 48A and displayed on or adjacent graphical representation 50. For example, therapy parameter input device 48A may display a palette that allows a user to choose different active electrode template options. In general, an active electrode template includes at least one cathode and at least one anode, and defines a spatial relationship between the anodes and cathodes, e.g., axially oriented or some other orientation. In some embodiments, one or more active electrode templates are randomly presented to a user for selection and testing. In other embodiments, a user may select individual cathodes and anodes from a palette to create an active electrode template. Additionally, a user may select more than one active electrode template to display on or adjacent graphical representation 50.

Upon selection of an active electrode template, the template may be placed at an arbitrary starting point on or adjacent graphical representation 50. For example, the template may appear near the top of graphical representation 50 in response to selection of the template. Alternatively, the user may drag the active electrode template or individual cathodes and anodes onto or adjacent graphical representation 50 via a user input device. In an alternative embodiment, a user may draw an active electrode template directly on or adjacent graphical representation 50. In the illustrated embodiment, active electrode template 52 is initially displayed near the top of graphical representation 50. The user input device used to drag or draw an active electrode template may be, for example, a pointing device, such as a mouse or stylus. In some embodiments, display may comprise a touch-screen.

The position of active electrode template 52 on or adjacent graphical representation 50 of the implanted electrodes provides a graphical representation of the therapy delivered from IMD 14 (FIG. 1) to patient 12 (FIG. 1) via the implanted electrodes. More specifically, active electrode template 52 and its position relative to graphical representation, as well as the other selected therapy parameters (e.g., amplitude, pulse rate, pulse width) represent the therapy that is delivered to patient 12 (FIG. 1) via IMD 14 (FIG. 1). Accordingly, processor 40 of programmer 11 may determine what stimulation parameter values to provide to IMD 14 for delivery of stimulation via implanted electrodes based on the position of active electrode template 52 relative to the electrodes of graphical representation 50. When the position of template 52 relative to the electrodes of graphical representation 50 is changed, the processor determines what adjustments to one or more stimulation parameters to implement to provide a therapy to patient 12 (FIG. 1) that matches the configuration and parameters displayed on display 46. Processor 40 of programmer 11 may use an algorithm to match (e.g., match within a specified degree of accuracy) the therapy delivered by IMD 14 to the view illustrated on display 46.

For example, processor 40 may determine an electrode configuration based on the position of active electrode template 52 relative to the graphical representation 50 of the electrodes implanted within patient 12. As discussed above, an electrode configuration defines the active subset of electrodes from among the implanted electrodes and their polarities. In some embodiments, when template 52 is positioned on or adjacent to particular electrodes of the graphical representation 50, the determined electrode configuration may comprise activating the corresponding implanted electrodes with the polarity indicated by the active electrode template.

In other cases, depending on the position of active electrode template 52, the actual electrode configuration determined by processor 40 may be different than active electrode template 52. For example, even though active electrode template 52 includes two anodes and one cathode, the electrode configuration determined by processor 40 based on the position of the template relative to graphical representation 50 may include more than three active implanted electrodes, and the active implanted electrodes may also have a spatial relationship different than that of template 52. Such differences between template 52 and the determined electrode configuration may be permitted or facilitated in some embodiments when, for example, the anodes and cathodes of template 52 are displaced from the electrodes of graphical representation 50. For example, processor 40 of programmer 11 may determine an electrode configuration such that delivery of electrical stimulation via the determined electrode configuration results in an electrical field including "virtual" anodes and cathodes, i.e., loci of positive and negative charge, at locations displaced from the physical implanted electrodes. The locations of the virtual anodes and cathodes relative to the physical implanted electrodes may substantially correspond to the locations of the anodes and cathodes of template 52 relative to the electrodes of graphical representation 50.

Additionally or alternatively, the amplitude may vary among each of the activated electrodes. Rather than simply being on or off, an electrode may be partially on. This may facilitate the creation of electrical fields including virtual electrodes, as well as permit complex shifting of an electrical field as the active electrode template 52 is moved relative to the graphical representation of implanted electrodes 50.

Figure 5A:
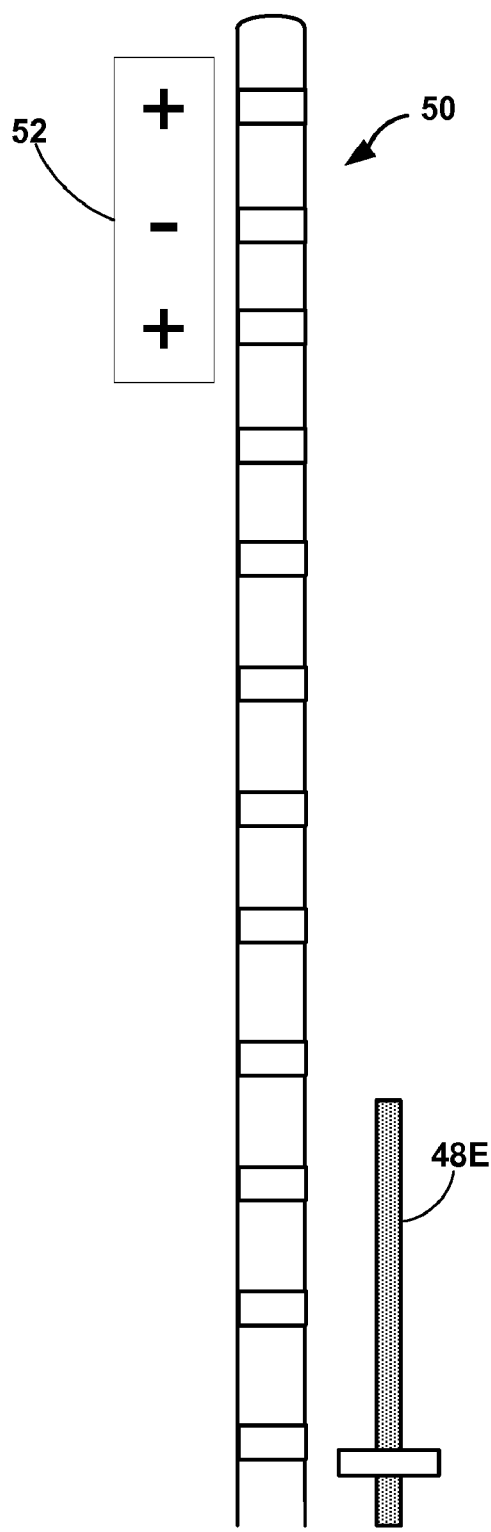
FIG. 5A illustrates a graphical representation of implanted electrode and an initial position of an active electrode template relative to the graphical representation.
Figure 5B:
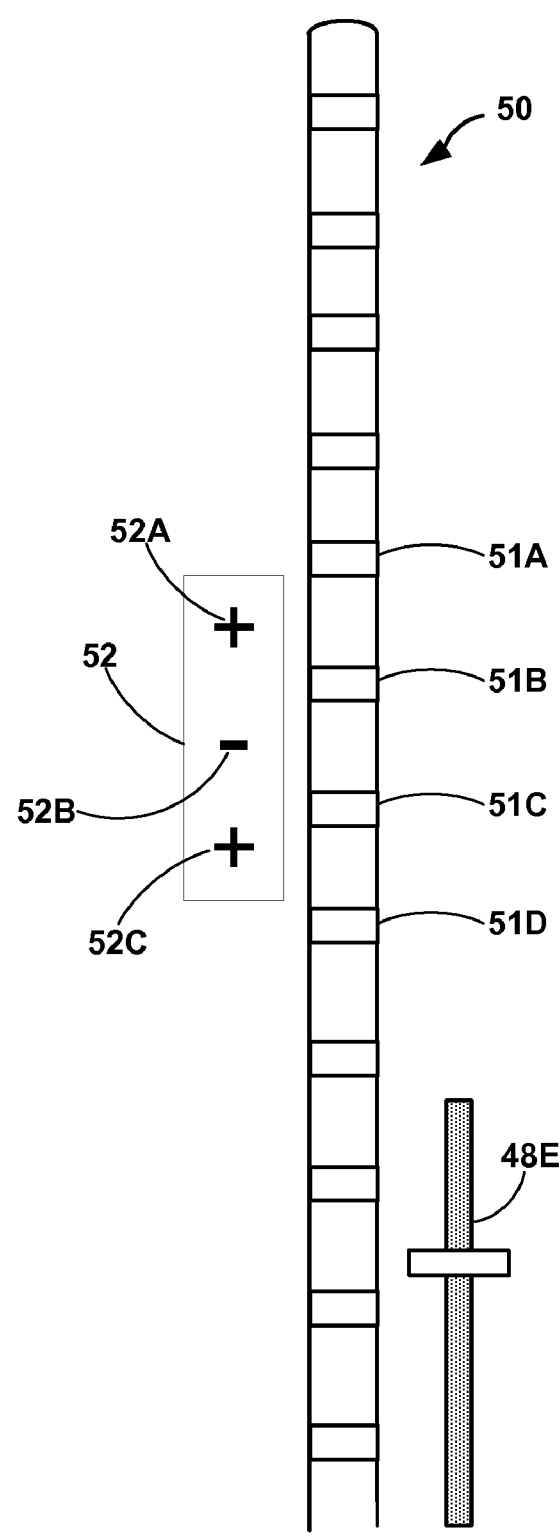
FIG. 5B illustrates a second active electrode template position relative the graphical representation of FIG. 5A.

In FIG. 5B, anodes 52A and 52C and cathode 52B of template 52 are displaced from electrodes 51A-51D of graphical representation 50. In some embodiments, the configuration of the implanted electrodes determined by programmer 11 based on the location of template 52 may comprise electrodes 51A and 51C activated as anodes and 51B as a cathode using the same amplitude for all three electrodes 51A-51C electrodes. In other embodiments, to more accurately represent the therapy displayed on graphical representation 50, a different, and possibly more complex, electrode configuration may be used to create virtual electrodes at the positions of anodes 52A and 52C and cathode 52B. Using vector addition, the programmer 11 may determine an electrode configuration in which the electrical field is the strongest at locations other than the locations of the activated electrodes, e.g., the locations corresponding to the locations of anodes 52A and 52C and cathode 52B of template 52 relative graphical representation 50. In this manner, the user may maintain a constant view of active electrode template 52 even though the actual electrode configuration used by IMD 14 (FIG. 1) may be different, e.g., more complex.

An algorithm used by processor 40 of programmer 11 to determine electrode configurations based on the position of template 52 relative to representation 50 may be developed based computer modeling of what electrical fields result from delivery of stimulation to tissue via various electrode configurations with various values for other stimulation parameters, such as pulse amplitude, width and rate. The computer modeling may be performed by a computer modeling system, such as the one available from the University of Twente.

When electrode pattern 52 is displayed on or adjacent graphical representation 50, a user may adjust the amplitude of the therapy delivered to patient 12 (FIG. 1) via input mechanism 48E to verify that the amplitude is set to a safe and effective level. The electrode combination, which is related to the position of electrode pattern 52 on graphical representation 50, and stimulation amplitude settings are tightly coupled. A comfortable stimulation amplitude for one electrode combination might be uncomfortable or imperceptible for a second electrode combination. A user may manually adjust the stimulation amplitude via input mechanism 48E at any time. Such an amplitude adjustment may change the net amplitude of the therapy delivered to patient 12 (FIG. 1). Since each active electrode of an electrode combination may have a unique amplitude in some embodiments, the amplitude delivered by each active electrode may be adjusted differently in response to a net amplitude adjustment.

Active electrode template 52 may be dragged from its initial position to other locations on or adjacent graphical representation 50 via a user input device. The user input device may function in a manner similar to that of a traditional mouse for a personal computer. For example, the user input device may control a cursor or the like, and may provide select, drag and drop functionality with respect to active electrode template 52.

FIG. 5A illustrates the first, initial active electrode template position and amplitude setting illustrated in FIG. 4, and FIG. 5B illustrates a second template position and amplitude setting. Active electrode template 52 may be dragged from the first position to the second position by positioning a positional input device over template 52 at the first position, depressing and holding a button on the positional input device once the input device is positioned over template 52, dragging electrode pattern to the second position by moving the mouse to the second position, and dropping electrode pattern 52 at the second position by releasing the button on the input device. The background software may update the therapy delivered by IMD 14 (FIG. 1) by determining an electrode configuration based on the position of electrode pattern 52 relative to graphical representation 50. Additionally, the user may adjust the amplitude of the therapy delivered by IMD 14 (FIG. 1) via input mechanism 48E, if the initial amplitude setting is not effective for the new electrode combination. In other embodiments, amplitude may automatically be adjusted for new electrode configuration determined for the second position of the template based on threshold values determined for the various implanted electrodes. As will be described in further detail below, dragging template 52 may include rotating the template about an axis point, which may be user selected.

Boundaries may be created to prevent a user from choosing a position for active electrode template 52 that would result in therapy parameter values not able to be provided by IMD 14 and the electrodes implanted within patient. For example, boundaries may prevent a user from selecting an unreasonable position for active electrode template 52 that can not be feasibly converted to an actual electrode configuration. In some embodiments, user interface 44 may prevent the user from positioning template 52 too far away from lead graphical representation 50. Additionally or alternatively, a warning may be displayed when template 52 is moved to and/or toward an unreasonable position.

In addition to adjusting stimulation parameter values when active electrode template is dropped in a new position, programmer 11 may adjust the therapy delivered by IMD 14 (FIG. 1) a plurality of times as active electrode template 52 is moved, e.g., dragged. Programmer 11 may, for example, adjust stimulation parameters when the template reaches certain predefined positions relative to representation 50. In other embodiments, programmer 11 may adjust stimulation parameters at a substantially fixed rate, which may include periodically determining the position of template 52 relative to the electrodes of graphical representation 50, determining an electrode configuration and/or other stimulation parameter values based on the position, and adjusting the stimulation delivered by IMD 14 by programming the IMD to deliver stimulation based on the determined configuration and/or other values.

In one embodiment, programmer 11 may adjust the therapy delivered by IMD 14 at constant time intervals. In this manner, the therapy update resolution is dependent upon the speed at which active electrode template 52 is moved. For example, if template 52 is moved from the first position illustrated in FIG. 5A to the second position illustrated in FIG. 5B, the number of times the therapy delivered by IMD 14 is adjusted depends on the speed at which template 52 is moved. In general, cutting the speed in half approximately doubles the number of times the therapy delivered by IMD 14 is adjusted when moved between the first and second position. Whereas, doubling the speed approximately halves the number of times the therapy delivered by IMD 14 is updated when moved between the first and second position.

Adjusting the therapy delivered by IMD 14 at constant time intervals allows the user to adjust resolution, e.g., the number of different parameter values tested and the magnitude of difference between the parameter values, simply by changing the speed at which he or she is dragging template 52. If a user would like to make a large change in the stimulation parameters, e.g., electrode configuration, the user may quickly move template 52, and the therapy delivered by IMD 14 may only be updated at a few times between the initial and resulting positions. If the user would like to tweak or fine tune the therapy delivered by IMD 14 by testing a variety of positions for template 52 within a small area, the user may change the position of template 52 at a slower speed to obtain better resolution and test more positions.

When active electrode template 52 remains at one location for a threshold period of time, programmer 11 may store the current stimulation parameters as a therapy program. In other embodiments, programmer 11 may prompt the user to decide whether or not to store a therapy program under such conditions. Alternatively, either the storing or prompting may occur in response to the user "dropping" template 52 after dragging the template.

FIG. 6A illustrates an alternate graphical representation electrodes implanted within a patient and initial active electrode template position. Graphical representation 54 represents a lead type that differs from the lead type depicted by graphical representation 50 and, more particularly, a paddle type lead with a plurality of electrodes arranged two-dimensionally as an array on a common surface. Input mechanism 48D (FIG. 4) may prompt the user for a variety of lead characteristics in order to present a graphical representation that matches the lead type and arrangement of electrodes implanted in patient 12 (FIG. 1).

Active electrode template 56 is shown at an initial position on graphical representation 54 in FIG. 6A. FIG. 6B illustrates a second template position relative to graphical representation 54. Template 56 may be dragged along locations on or adjacent graphical representation 54, and programmer 11 may adjust the stimulation delivered by IMD 14 as template 56 is moved. Additionally, template 56 may be rotated about an axis point. For example, the user may select an axis point by any appropriate means (e.g., clicking on a point on active electrode template 56 or graphical representation 54) and rotate template 56 about that point. For example, selecting axis point 58 on template 56 in FIG. 6A and rotating template 56 in the direction indicated by arrow 60 may yield the orientation of template 56 illustrated in FIG. 6B. In some embodiments, rotation of an active electrode template 56 may be used to fine tune the stimulation delivered by IMD 14.

Figure 7:
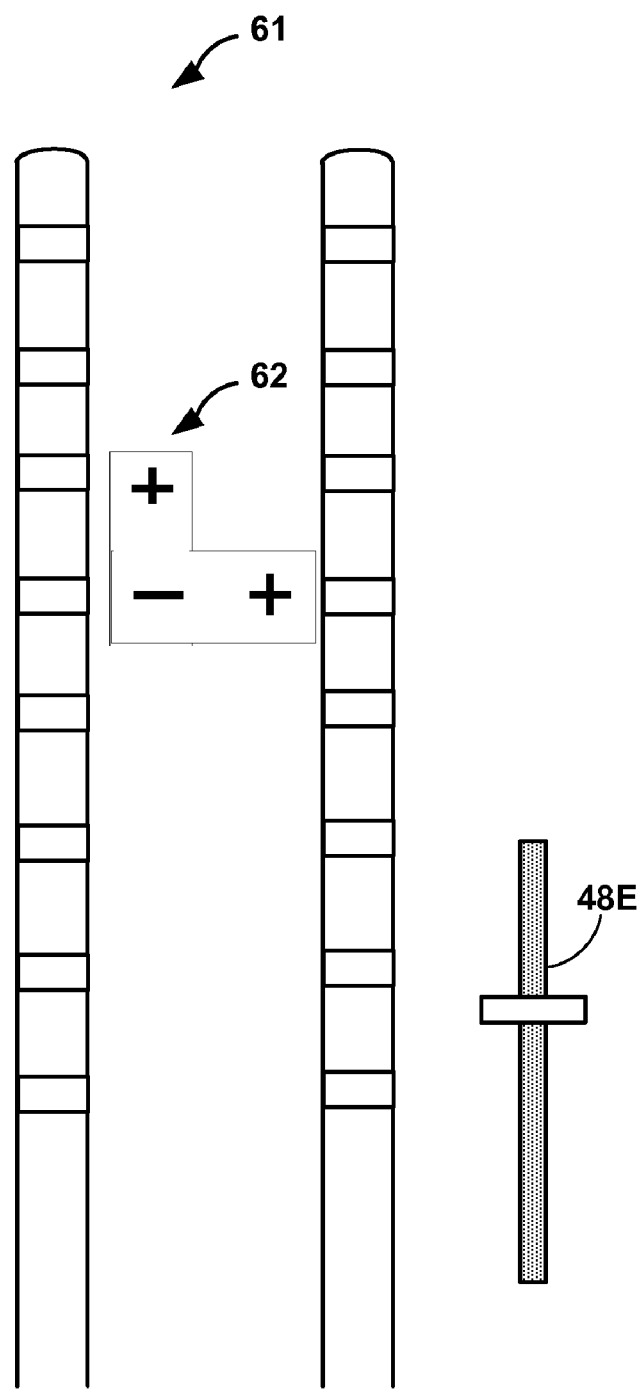
FIG. 7 illustrates another example of a graphical representation of implanted electrodes and an active electrode template.

FIG. 7 illustrates another example of a graphical representation 61 of implanted electrodes and an active electrode template 62. As illustrated by the example of FIG. 7, graphical representation 61 of implanted electrodes may include electrodes on more than one lead. Further, active electrode template 62 defines a non-axial spatial relationship of the constituent anodes and cathode relative to each other.

In embodiments in which a plurality leads are implanted within patient in proximity to each other, programmer 11 may display graphical representation that includes the electrodes on the plurality of leads. A user of programmer 11 may position an active electrode template between or across the leads to test electrode configurations including active electrodes on a plurality leads, delivery of stimulation through which may result in electrical fields and, in some cases, virtual electrodes, between the leads. In some embodiments, the electrodes on more than two implanted leads may be graphically represented to, for example, allow transverse (relative to the axis defined by the lead body) tripole electrode configurations to be tested.

Figure 8:
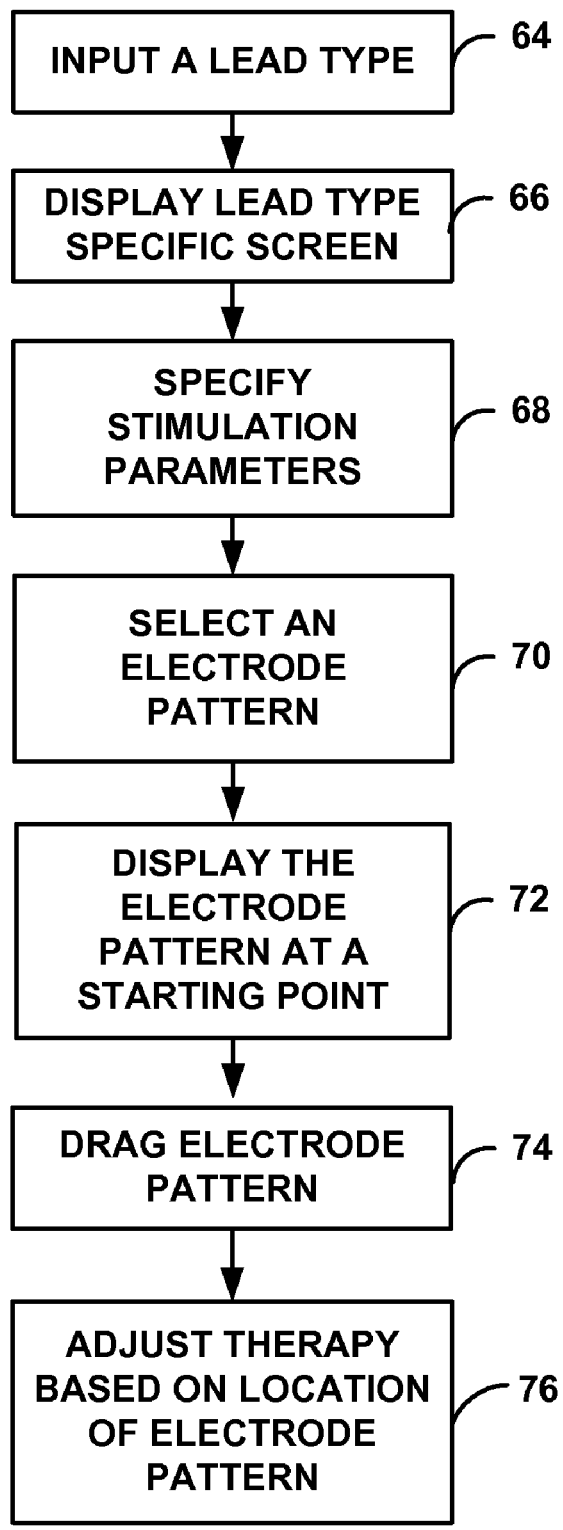
FIG. 8 is a flowchart illustrating one embodiment of utilizing the user interface of FIG. 4.

FIG. 8 is a flowchart illustrating one embodiment of utilizing a user interface 44 (FIG. 4). A user may input a lead type via input mechanism 48D (64). The user may select parameters such as the number of leads, the shape of the lead body (e.g., cylindrical or paddle), the type of electrodes (e.g., ring, segmented, or both), the number of electrodes, and/or the number of rows and/or columns of electrodes to help define the lead type. Once the lead type is defined, programmer 11 displays a screen illustrating graphical representation of the implanted electrodes on one or more leads according to the selected lead parameters (66). The user may define the electrical stimulation to be delivered to patient 12 (FIG. 1) by specifying stimulation parameters, such as pulse width and pulse rate, via input mechanisms 48 (68).

The user may also select an active electrode template comprising at least one cathode and at least one anode (70). The template may be selected from a palette or drawn on or adjacent graphical representation 50. After selection of the template, the template is displayed at a starting point on or adjacent the graphical representation (72). The starting point for the active electrode template may be arbitrary and may appear near the top of the graphical representation of the implanted electrodes in response to selection of template. Alternatively, the user may drag the active electrode template onto or adjacent the graphical representation. In an alternative embodiment, a user may draw an active electrode template directly on or adjacent to the graphical representation of the implanted electrodes.

In order to test various electrode configurations, active electrode template may be dragged along the graphical representation of the implanted electrodes (74). As the template is dragged, programmer 11 may adjust the stimulation delivered by IMD 14 based on the location of the active electrode template relative to the graphical representation of the implanted electrodes (76). As the template is moved and the stimulation delivered by IMD 14 is adjusted, it may be necessary to adjust the amplitude of the stimulation. A user may adjust the amplitude of the stimulation at any time. For example, the user may receive feedback from patient 12 (FIG. 1) and adjust the amplitude as needed.

Figure 9:
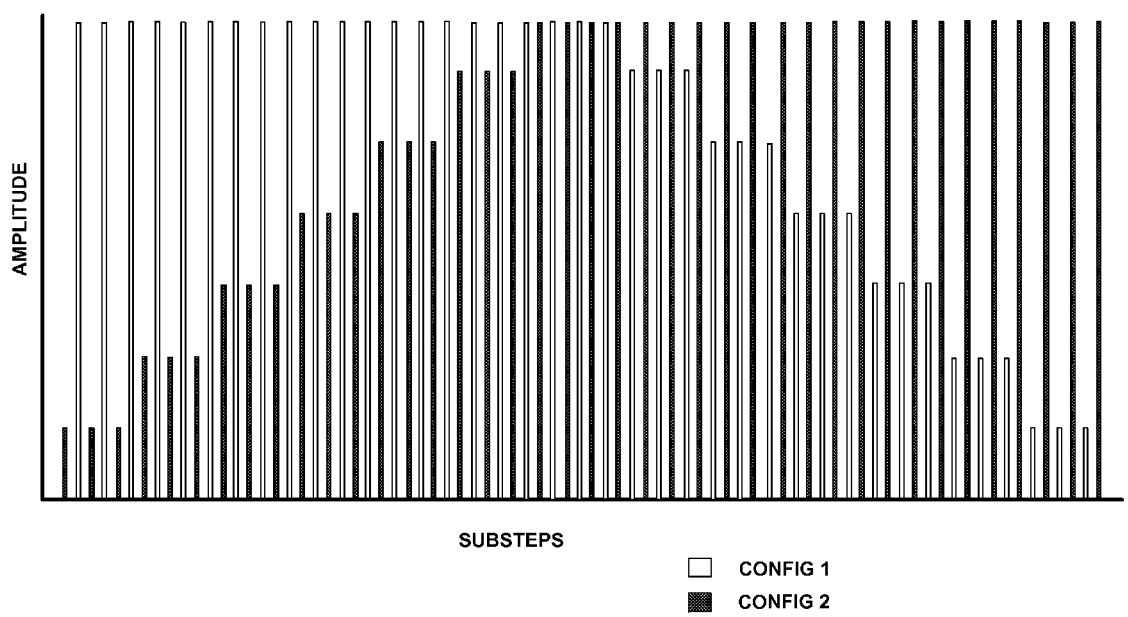
FIG. 9 is a timing diagram illustrating adjustment of the electrode configuration for stimulation based on repositioning an active electrode template relative to a graphical representation of implanted electrodes.

FIG. 9 is a timing diagram illustrating adjustment of the electrode configuration for stimulation based on repositioning an active electrode template relative to a graphical representation of implanted electrodes. Rather than abruptly switching from one electrode configuration to a new configuration, the stimulation energy may be shifted from the old configurations to the new configurations by delivering stimulation energy to different electrode configurations on a time-interleaved basis. The IMD may gradually transition from a first electrode combination to a second electrode combination in incremental steps. For example, the IMD or programmer may incrementally decrease an amplitude of a first electrode combination over a series of time slots while concurrently increasing an amplitude of a second electrode combination over a series of alternating time slots. Alternatively, as illustrated in FIG. 9, the amplitude of the first electrode configuration may be maintained at a target level while the amplitude of the second electrode configuration is incrementally increased. Then, the amplitude of the first electrode configuration may be incrementally decreased after the amplitude of the second electrode configuration has reached the target level. In either case, the IMD may interleave the stimulation pulses provided by the first and second electrode configurations in time at a sufficiently high frequency so that the patient perceives the physiological effects of the stimulation energy as smooth, or nearly simultaneous or overlapping in time. Each time slot may include a single pulse or multiple pulses from a given electrode combination. Interleaving programming in this manner is described further detail in commonly-assigned U.S. patent application Ser. No. 11/401,100, filed Apr. 10, 2006, issued as U.S. Pat. No. 7,519,431 on Apr. 14, 2009, and entitled, "SHIFTING BETWEEN ELECTRODE COMBINATIONS IN ELECTRICAL STIMULATION DEVICE," which is hereby incorporated by reference in its entirety. As described in application Ser. No. 11/401,100, interleaving electrode configurations in this manner may allow a single stimulation pulse generator, e.g., a single channel pulse generator, to be, in effect, multiplexed across the electrode combinations.

In other embodiments, a plurality of voltage or current sources may be used to effect smooth transitions between electrode configurations by delivering stimulation via a plurality of electrode configurations substantially simultaneously during the same pulse or time slot. An example of such techniques is described in U.S. Pat. No. 6,909,917 to Woods et al. The amplitudes for the new and old configurations may be increased and decreased in any of the ways described above.

Various embodiments of the invention have been depicted and described. However, those of ordinary skill in the art will recognize that various modifications may be made to these embodiments without departing from the scope of the claims. For example, although graphical representations of implanted electrodes have been depicted herein as including representations of the leads carrying the electrodes, the invention is not so limited. In some embodiments, the graphical representation may instead include a representation of the electrodes without their leads, which may or may not include an accurate representation of the spatial relationship of the electrodes on the leads.

Further, although depicted as including positive and negative symbols, active electrode templates are not so limited. In other embodiments various shapes, colors or symbols may be used to represent individual electrodes or groups of electrodes (e.g., bipoles) in an active electrode template. These and other embodiments are within the scope of the following claims.

The invention claimed is:

1. A method for programming a single channel pulse generator of an implantable medical device, the method comprising:
    displaying a graphical representation of a plurality of electrodes implanted within a patient on at least one medical lead;
    displaying an active electrode template at a first position relative to the graphical representation of the electrodes, the active electrode template including one or more anodes and one or more cathodes and defining a spatial relationship of the one or more anodes and one or more cathodes;
    receiving input from a user moving the active electrode template to a second position relative to the graphical representation of the electrodes; and
    in response to the input moving the active electrode template, adjusting at least one parameter of electrical stimulation delivered from the single channel pulse generator to the patient via at least a subset of the implanted electrodes based on the second position of the active electrode template relative to the graphical representation of the electrodes on the stimulation lead,
    wherein at least one of the one or more anodes and one or more cathodes of the active electrode template is displaced from the electrodes of the graphical representation when the active electrode template is located at the second position.

2. The method of claim 1, wherein each of the one or more anodes and one or more cathodes of the active electrode template is displaced from the electrodes of the graphical representation when the active electrode template is located at the second position.

3. The method of claim 1, wherein adjusting the parameter of electrical stimulation delivered by the single channel pulse generator comprises adjusting at least one of which of the implanted electrodes are active or polarities of active ones of the implanted electrodes based on the second position of the active electrode template relative to the graphical representation of the electrodes.

4. The method of claim 3, wherein a number of active implanted electrodes subsequent to the adjustment based on the second position of the active electrode template is different than a number of electrodes in the active electrode template.

5. The method of claim 3, wherein the polarities of active implanted electrodes subsequent to the adjustment based on the second position of the active electrode template are different than polarities of the active electrode template.

6. The method of claim 3, wherein a spatial relationship of active implanted electrodes subsequent to the adjustment based on the second position of the active electrode template is different than the spatial relationship of electrodes in the active electrode template.

7. The method of claim 3, wherein each active implanted electrode is fully on, and each inactive implanted electrode is fully off.

8. The method of claim 1, wherein adjusting the parameter of electrical stimulation delivered by the single channel pulse generator comprises adjusting the potentials of implanted electrodes based on the second position of the active electrode template relative to the graphical representation of the electrodes.

9. The method of claim 1, wherein receiving input from a user positioning the active electrode template at a second position comprises receiving input rotating the active electrode template about an axis point.

10. A system for programming a single channel pulse generator of an implantable medical device, the system for programming comprising:
    a display that displays a graphical representation of a plurality of electrodes implanted within a patient on, and coupled to the pulse generator by, at least one medical lead, and displays an active electrode template at a first position relative to the graphical representation of the electrodes, the active electrode template including one or more anodes and at one or more cathodes and defining a spatial relationship of the one or more anodes and one or more cathodes;
    a user input device; and
    a processor that:
        receives input from a user moving the active electrode template to a second position relative to the graphical representation of the electrodes via the user input device, and
        in response to the input moving the active electrode template, adjusts at least one parameter of electrical stimulation delivered from the single channel pulse generator to the patient via at least a subset of the implanted electrodes based on the second position of the active electrode template relative to the graphical representation of the electrodes,
    wherein at least one of the one or more anodes and one or more cathodes of the active electrode template is displaced from the electrodes of the graphical representation when the active electrode template is located at the second position.

11. The system of claim 10, wherein each of the one or more anodes and one or more cathodes of the active electrode template is displaced from the electrodes of the graphical representation when the active electrode template is located at the second position.

12. The system of claim 10, wherein the processor adjusts at least one of which of the implanted electrodes are active, or polarities of active ones of the implanted electrodes, based on the second position of the active electrode template relative to the graphical representation of the electrodes.

13. The system of claim 12, wherein a number of active implanted electrodes subsequent to the adjustment based on the second position of the active electrode template is different than a number of electrodes in the active electrode template.

14. The system of claim 12, wherein the polarities of active implanted electrodes subsequent to the adjustment based on the second position of the active electrode template are different than polarities of the active electrode template.

15. The system of claim 12, wherein a spatial relationship of active implanted electrodes subsequent to the adjustment based on the second position of the active electrode template is different than the spatial relationship of electrodes in the active electrode template.

16. The system of claim 10, wherein adjusting the parameter of electrical stimulation delivered by the single channel pulse generator comprises adjusting the potentials of implanted electrodes based on the second position of the active electrode template relative to the graphical representation of the electrodes.

17. The system of claim 10, wherein receiving input from a user positioning the active electrode template at a second position comprises receiving input rotating the active electrode template about an axis point.

18. The system of claim 10, wherein the user input device comprises the display.

19. A non-transitory computer-readable storage medium comprising instructions that cause a processor to: Control display of a graphical representation of a plurality of electrodes implanted within a patient on at least one medical lead; control display of an active electrode template at a first position relative to the graphical representation of the electrodes, the active electrode template including one or more anodes and one or more cathodes and defining a spatial relationship of the one or more anodes and one or more cathodes; receive input from a user moving the active electrode template to a second position relative to the graphical representation of the electrodes; and in response to the input moving the active electrode template, adjust at least one parameter of electrical stimulation delivered from a single channel pulse generator of an implantable medical device to the patient via at least a subset of the implanted electrodes based on the second position of the active electrode template relative to the graphical representation of the electrodes, wherein at least one of the one or more anodes and one more cathodes of the active electrode template is located at the second position.

* * * * *